United States Patent [19]

Dulbecco

[11] Patent Number: 4,593,002
[45] Date of Patent: Jun. 3, 1986

[54] VIRUSES WITH RECOMBINANT SURFACE PROTEINS

[75] Inventor: Renato Dulbecco, La Jolla, Calif.

[73] Assignee: Salk Institute Biotechnology/Industrial Associates, Inc., San Diego, Calif.

[21] Appl. No.: 338,416

[22] Filed: Jan. 11, 1982

[51] Int. Cl.[4] ............ C12N 15/00; C12N 7/00; C12N 7/02; C12N 1/00; C12P 21/00; C12P 21/02; C12P 21/04; C12P 19/34; A61K 39/12; A61K 37/00

[52] U.S. Cl. .................... 435/172.3; 435/68; 435/70; 435/71; 435/91; 435/235; 435/239; 435/317; 935/12; 935/31; 935/32; 935/65; 424/89; 424/93

[58] Field of Search ............ 435/68, 70, 172, 71, 435/91, 172.3, 235, 239, 317; 935/12, 31, 32, 65

[56] References Cited

U.S. PATENT DOCUMENTS 4,237,244  12/1980  Cohen et al. ............ 435/172
4,428,941   1/1984  Galibert et al. .......... 935/12
4,442,205   4/1984  Hamer et al. ............ 935/12

FOREIGN PATENT DOCUMENTS 2070621  9/1981  United Kingdom ............ 935/12

OTHER PUBLICATIONS

Fey et al: J. Virol. 30: 201 (1979).
Grodzicker: in *DNA Tumor Viruses*, Tooze (ed.), 1981, Cold Spring Harbor Laboratory, pp. 577–581.
Van Roy et al: J. Mol. Biol. 126: 691 (1978).
Broome et al: Proc. Natl. Acad. Sci. USA 75: 2746 (1978).
Blattner et al: Science 196: 161 (1977).
Sveda et al., Proc. Natl. Acad. Sci. USA, vol. 78, No. 9, pp. 5488–5492, Sep. 1981.
Charnay et al., Nature, vol. 286, pp. 893–895, Aug. 1980.
Moriarity et al., Proc. Natl. Acad. Sci. USA, vol. 78, No. 4, pp. 2606–2610, Apr. 1981.
Walter et al., Proc. Natl. Acad. Sci. USA, vol. 77, No. 9, pp. 5197–5200, Sep. 1980.

*Primary Examiner*—Blondel Hazel
*Assistant Examiner*—James Martinell
*Attorney, Agent, or Firm*—Fitch, Even, Tabin & Flannery

[57] ABSTRACT

Foreign protein segments having specific medically or commercially useful biological functions are incorporated in surface proteins of viruses. The viruses with the incorporated protein segments are convenient agents for introducing the protein segments into animals, such as humans, and are thus useful as vaccines. Small segments of an original protein exhibiting desired functions are identified, and a DNA fragment having a nucleotide base sequence encoding that segment of the protein is isolated from an organism or synthesized chemically. The isolated DNA fragment is inserted into the DNA genome of a virus in a manner such that the inserted DNA fragment expresses itself as the foreign segment of a surface viral protein and in such a way that neither the function of the protein segment nor the function of any viral protein critical for viral replication is impaired.

8 Claims, No Drawings

VIRUSES WITH RECOMBINANT SURFACE PROTEINS

This invention relates generally to the introduction of protein segments having particular biological functions into animals, including human beings. More particularly, this invention relates to the use of viral carriers to introduce into organisms small peptide segments possessing certain functions normally found on larger protein molecules.

BACKGROUND OF THE INVENTION

Many biological functions, including antigenic functions, hormonal functions, enzymatic functions, and cell-regulatory functions are provided by proteins. Proteins consist of long chains of amino acids in a particular sequence. The above-mentioned functions are typically attributable to rather limited segments of the protein comprising short sequences of amino acids. The rest of the protein molecule often serves as a carrier for the functional segment or segments. The carrier segments protect the functional segments of the protein and present the functional segments to substrates in an orientation which promotes activity. In addition, certain properties of the functional segments of the protein are only able to take effect when the short sequences of amino-acids comprising the functional segments are connected to a longer protein chain. For example, immune response to a particular short amino-acid sequence generally requires that the short sequence be coupled to an extended molecule. In principle, the carrier segments of the protein could be replaced with a variety of other carrier segments without altering the properties of the functional protein segment. Such substitutions may effect certain distinct advantages, as will become clear, in the utilization of functional protein segments for commercial or medical purposes, such as the production of useful vaccines.

In particular, it will be seen that viral proteins are particularly suited to being exploited as carriers for small amino-acid sequences possessing useful functions. One particularly useful function of proteins, typically attributable to limited segments of a protein, is the ability to induce an immune response. When injected, inhaled, ingested, or otherwise placed into a live animal, a foreign protein, i.e., one not naturally present in the host animal, elicits an immune response. The immune response consists of many different concerted processes in the animal, including the production of antibodies, which attack the foreign protein and thereby protect the animal from infection by a carrier of the foreign protein. Importantly, an additional feature of the immune response is a form of biological memory such that a second exposure to the same foreign protein results in a quicker and much stronger immune response. This is the principle of vaccination which is an important part of modern medicine.

It has been found that effective immune responses are induced by small segments of proteins when they are attached to large carrier segments even if the carrier segments are not naturally of the same protein. Vaccinations with such proteins having a functional segment from one protein attached to unnatural carrier segments results not only in protection against further injection of the hybrid protein but also against the original protein from which the functional segment was obtained.

Typically, vaccines are produced in laboratories by preparing agents having substantially reduced pathogenicity with respect to disease-causing viruses that contain protein segments that induce an immune response. These agents are either strains of microorganisms which produce only mild diseases or else are chemically inactivated microorganisms. The vaccines are introduced into an animal to induce an immune response in the injected animal; however, there have been problems with such vaccines. Many infectious agents are difficult or impossible to grow under controlled conditions, and those which are grown and then inactivated present the possiblity of partial escape from the inactivation process which poses an appreciable risk to the vaccinated animal. With weakened strains of infectious microorganisms, the risk of natural mutation to more dangerous forms is inherent, similarly potentially endangering the vaccinated animal. Moreover, all the techniques involved in the production of such vaccines are time-consuming and expensive.

Accordingly, it is advantageous to use, as vaccines, immunogenic (immune-response-producing) protein segments obtained from infectious agents attached to unnatural carriers in place of the infectious agents themselves. In accordance with one aspect of the invention, viral proteins are particularly useful as carriers, and immunogenic protein segments are inserted into viral proteins in such a way that the viruses carry the segments so that they will be exposed to the immune system of a vaccinated animal without the immunogenic protein segments interfering with viral viability or reproduction. Several kinds of viruses can be used to carry immunogenic protein segments, each with distinct advantages. Among these are DNA-containing bacteriophages, nonpathogenic DNA-containing animal viruses and nonpathogenic enveloped RNA-containing influenza viruses.

DNA-containing bacteriophages, such as lambda phage, are viruses which infect bacteria. These viruses multiply to great numbers in bacteria, and they may be produced at small cost, are not pathogenic for animals or humans and can be introduced by ingestion, inhalation, or injection. Nonpathogenic animal viruses, such as the DNA-containing adenoviruses and the enveloped RNA-containing influenza viruses, replicate in human or animal cells, resulting in inapparent or inconsequential infections. These can thus be safely introduced by injection, ingestion or inhalation.

Proteins exposed on the surface of these viruses are preferred as foreign immunogenic protein segments. Surface proteins are capsid proteins in the case of non-enveloped viruses and trans-membrane proteins in the case of enveloped viruses.

When an immunogenic protein segment is incorporated in an exposed manner in a surface virus protein, the entire virus serves as an extended carrier. The virus carrier retains the ability to replicate while the incorporated foreign protein segment has the potential for inducing the specific immune response. The virus carrier also retains its biological functions, contributing to protein stability.

Other types of viruses may also be used to advantage as carriers in accordance with the invention. Furthermore, short protein segments with functions other than the capacity to stimulate immune responses may be incorporated as viral surface protein segments by the methods of the invention.

The joining of protein segments with specific functions to protein carriers may be accomplished by taking advantage of recent advances in understanding the genetic code, molecular biological processes and the technology of recombinant DNA genetics. The amino-acid sequences of cellular proteins, as well as most viral proteins, are determined by genes which are segments of deoxyribonucleic acids (DNA) sequenced according to the genetic code. The particular sequence of amino-acids is synthesized in accordance with the sequence of codons (triplets of nucleic acid subunits) in the DNA. Insertion of foreign DNA sequences into the DNA of a host organism, under certain appropriate conditions, results in the expression of the amino-acid sequence specified by the inserted, foreign DNA sequence.

Recombinant DNA technology allows such manipulations to be conveniently carried out. Sequences of DNA encoding a particular protein or protein segment may now be easily isolated and purified in large enough amounts to use biochemically. These sequences can then be cut in specific places, using enzymes known as restriction endonucleases, and spliced together with other purified fragments using DNA ligases. These recombinant molecules can then be put into living organisms, such as bacteria or higher cells.

It would be desirable to utilize the recombinant techniques which have been developed to incorporate protein segments having specific functions in surface viral proteins to provide useful agents for commercial and medical processes.

It is an object of the present invention to provide a method for attaching useful protein segments to virus carriers.

Another object of the invention is to provide viral carriers of immunogenic protein segments for inducing immune responses in animals. Specifically it is an object to produce new, safer vaccines. A further object is to provide improved vaccinations of mammals, including humans.

SUMMARY OF THE INVENTION

Foreign protein segments are incorporated as exposed segments of surface viral proteins in a manner which does not effect the reproductive viability of the virus. Viruses with recombinant or foreign protein segments are useful for introducing the function, e.g., immune response inducing, of the foreign protein segment into an animal, such as humans. The foreign protein segment is incorporated by inserting a DNA fragment with a nucleotide base sequence coding for the protein segment into the viral genome in a manner in which the inserted DNA fragment expresses itself as an exposed segment of a surface viral protein.

To incorporate the foreign DNA fragment, the viral genome, or a portion thereof, is inserted into a cloning vector which, in turn, is introduced into a host microorganism to produce multiple copies of the recombinant cloning vector. The foreign DNA fragment is isolated and inserted into the recombinant cloning vector at an appropriate location within the viral DNA genome portion. The foreign DNA segment-containing viral DNA genome portion is isolated from the cloning vector, and the complete viral genome is reconstructed. The viral genome containing the foreign DNA fragment is packaged as a complete virus; after infecting cells, it will generate progeny in which the foreign protein segment is expressed as a portion of one of its surface proteins.

DETAILED DESCRIPTION OF THE PREFERRED EMBODIMENTS

In accordance with the present invention, functional protein segments are incorporated in viral protein carriers.

Herein the term "virus" shall include bacteria-infecting viruses including bacterial viruses or phages as well as animal-infecting viruses. The term "recombinant protein" is used herein to refer to a protein which is the expression product of a gene containing a foreign nucleotide base sequence, the recombinant protein including an amino-acid sequence which is foreign or unnatural to the protein of the virus.

In general, the method of the protein segment incorporation may be broken down into a series of seven discrete steps, which need not be performed strictly in the order given.

The first step is the selection of a virus having a protein appropriate for use as a carrier of the functional foreign protein segment. The selection of the particular virus depends, in part, on the ultimate use of the protein. If, for example, a vaccine for immunizing cattle is desired, an appropriate virus would be one capable of replicating in cattle without causing serious pathological effects. Moreover, it may be appropriate to use a strain of virus to which the cattle in question have had little or no previous exposure to assure that strong, primary immune reactions develop. Other considerations of virus selection will become apparent from the examples given below and from facts generally known about bacterial and animal viruses.

Once a virus has been selected, a carrier protein of choice is based upon examination of the known molecular biology of that virus. Suitable carrier proteins are on the external surface of the virus, which are nonessential for viability and replication of the virus or which contain regions (where the functional protein segment will be incorporated) that are nonessential for viability and replication. Examples of such appropriate nonessential viral proteins are the D and E gene products of the bacteriophage λ, the neuroaminidase protein of orthomyxoviruses; and hexon and protein IX of the adenoviruses.

The second step of the method is to insert the DNA genome of the chosen virus, or a portion of the DNA genome containing the gene coding for the chosen viral carrier protein, into a cloning vector, such as a plasmid vector. The plasmid vector allows the DNA of the virus to be propagated in bacteria wherein a large number of copies of this DNA are produced for further manipulations.

The virus genome portion is inserted into a plasmid by standard techniques. In brief, the plasmid, which is a circle of a particular DNA sequence, is cut at known sites with one or more restriction endonucleases. The same enzymes are used to cut the viral genome at specific sites chosen to contain the gene of interest between them, the sites of cutting being determined by the particular restriction enzymes used. As is well known, cutting two different pieces of DNA with the same restriction enzyme leaves fragment ends which stick to each other by base pair hydrogen bonding and which may be covalently joined by the enzyme T4-DNA ligase. If the sites of cutting necessitate the use of different restriction enzymes, the ends may be rendered compatible by treatment with the enzyme S1 or the Klenow fragment of DNA Pol I followed by the addition of short DNA segments called linkers.

Once the compatible viral genome portion is joined to the plasmid, one of the plasmid genes is typically destroyed. The destroyed gene, in general, is one that codes for a drug resistance. Plasmids usually carry several such genes that encode for proteins which convey resistance to different drugs. This provides an easy method for screening for a successfully recombined plasmid. The plasmid is put or "transformed" into bacteria, and then colonies of bacteria are screened for various drug resistances. Multiple copies of the recombinant plasmid are obtained from lysing the cell colony.

The third step consists of isolating a DNA fragment having the nucleotide base sequence coding for the functional sequence of amino acids to be incorporated as the foreign protein segment of the viral protein. Such DNA fragments are obtained from DNA cloned in a vector or are otherwise prepared in pure form. The gene coding for the entire functional protein is isolated in its entirety by cutting with restriction enzymes. The desired DNA fragment is then isolated by separating various DNA fragments by standard techniques, generally by electrophoresis through an agarose or acrylamide gel, but also by other means, such as columns or gradients.

Under certain conditions, the functional segment of the protein in question may not be known in advance. In such case, many fragments of the gene are generated with restriction enzymes. The mixture of fragments is then used in place of a purified DNA fragment which would otherwise be isolated, and a recombinant virus having the correct DNA fragment is obtained in the final step of the method when a functional screening is performed on the recombinant viruses as described below.

The DNA fragments coding for the functional protein segment are further prepared by joining them to appropriate linkers of various lengths. The type of linker is chosen to be compatible with the enzyme used to cut the viral gene in the fourth step. Linkers of various lengths are used in order to place at least some of the DNA fragments in the proper reading frame (so that three-nucleotide codons specifying amino acids are incorporated in the viral protein in phase with the codons of the viral DNA) and also to allow some flexibility in the recombinant protein, e.g., to assure that, in at least some of the recombinant proteins, the foreign segment is exposed in a manner which promotes its functioning. The fragments are joined to the linkers by first treating with an enzyme, such as S1 or the Klenow fragment of DNA Pol I, followed by joining with T4 DNA ligase. Excess linkers are removed, typically with a column.

The fourth step is to cut the viral genome portion to prepare it for the insertion of the foreign DNA fragment coding for the functional protein segment, and then to attach the two together in a productive way. If nonessential portions of the viral protein are known, an enzyme for cutting in that region of the DNA is used; otherwise a variety of enzymes cutting in different places in the viral gene are utilized. If the enzymes cut more than once in the viral gene, a partial digestion is performed, and DNA molecules with single cuts existing in the region of choice are isolated by electrophoresis through a gel. Once the plasmid-bound viral DNA is cleaved, it is joined to the earlier prepared foreign DNA fragment from step three with T4 DNA ligase to produce a plasmid which contains the remainder of the original plasmid, at least a portion of the viral genome and the the foreign DNA fragment within the viral genome portion. This modified plasmid is introduced by transformation into cells, typically of the same culture that was transformed in step 2, to produce multiple copies of the modified plasmid. Multiple copies of the plasmid are obtained from the culture lysate.

The fifth step of the method is to reconstruct the viral genome with the desired foreign DNA fragment inserted. The viral DNA genome portion with the incorporated foreign DNA fragment is released from the plasmid by digestion with the same restriction enzyme or enzymes used for preparing the viral DNA fragment for insertion into the plasmid in step two. If only a portion of the virus genome was inserted (rather than the entire viral genome), the virus is reconstructed by joining with other fragments in a series of well known steps, each using the enzyme T4 DNA ligase followed by purifying accurately joined fragments.

In a sixth step, the viral genome is packaged to produce an intact infectious virus with a complete protein coat. The packaging procedure depends upon the virus involved. Bacteriophage DNA, such as lambda phage, is packaged into viruses in vitro by well known reactions using purified phage extracts. Animal virus genomes are placed into cells, typically by a technique known as DNA-calcium phosphate coprecipitate transfection. Precipitates made by mixing DNA, calcium chloride and phosphate buffer are known to be taken up by animal cells. Once in the cells, the viral DNA produces specific RNAs, and the RNA's direct the synthesis of proteins from which the intact viruses are ultimately formed.

If packaged in vitro from phage extracts, the packaged viruses are transformed into a host cell culture in which the packaged virus strain reproduces. If packaged by transfection, viruses are reproduced in the transfected culture. By growth in culture, substantial copies of recombinant viruses are obtained.

The packaging and reproduction of recombinant viruses constitutes a selection for viral genomes which have been reconstructed in such a way that the resulting viruses are reproductively viable. It is to be appreciated that virus genomes, which produce the protein coat of the complete virus and which are reproductively viable as complete viruses, may represent only a portion of the recombinant DNA products of the process. Recombinant genomes missing necessary genome segments or having necessary genome segments in the wrong reading frame do not form the protein coat or do not reproduce if packaged. After packaging and reproduction of correctly recombined virus genomes, incorrectly recombined genomes are either lost or represent an insignificant portion of the recombinant viruses. Packaged, reproductively viable viruses can be seen by standard methods, such as plaque assays, and positive plaque assays are indicative of successful genome recombination. Some of the successfully recombined genomes contain the foreign DNA fragment, and some of these express the function of the foreign protein segment.

The final step of the invention consists of screening individual plaques of viruses from step six (each representing an independent recombinant) for the functional incorporated protein segment. The particular screening procedure depends on the type of function desired from the recombinant virus. Standard assays exist for many hormonal and enzymatic functions which may be desired. In the case of assaying for the ability to induce an immune response, the plaques are screened with antiserum raised against the original protein. Viruses are obtained and purified from duplicates of plaques sensitive to the antiserum, and the viruses are injected into host animals, e.g., rabbits. Antibodies produced by the animal against the injected virus are, finally, tested for the ability to cross-react with the original protein. The induction of antibody production to the original protein by the virus is conclusive proof that the virus incorporates at least an immune response-inducing segment of the original protein in a manner that the segment is exposed to the immune system of the host animal.

Because the virus incorporating the exposed recombinant protein segment is known to induce an immune response, it is useful as a vaccine, provided that it remains substantially non-pathogenic and provided that the immune-response the virus induces results in effective neutralization of the infectious agent which naturally carries the immune-response-inducing protein segment. Because the virus into which the foreign protein is incorporated is in itself non-pathogenic, it is generally true that the virus with the recombinant protein segment is non-pathogenic as well, but this must be ascertained in each case. Whether the virus having the recombinant protein segment induces an immune response that counteracts the infectious agent must also be determined in each case, and an effective dose is determined for those viruses (vaccines) which do induce immunity to the infectious agent.

Viruses having recombinant protein segments demonstrating effectiveness as vaccines are grown in appropriate cell cultures, and the viruses are recovered from lysates of such cultures. The method of administering the vaccine will vary according to the infectious agent being vaccinated against but is well known in the art; vaccines produced according to the invention may be administered along with a pharmaceutically acceptable diluent by injection, by ingestion through the mouth, nose, eye, ear or other body orifice, or by inhalation. The virus is admixed with an appropriate carrier suitable for the intended method of introduction. For example, viruses having recombinant protein segments may be admixed with an aerosol and administered to animals through the air for inhalation. An effective amount of the virus is administered as is well known in the art. Generally, viruses which contain a surface protein segment that induces an immune response to infectious agent are administered in an amount of about $10^9$–$10^{10}$ particles per kilogram of body weight of the animal.

The usefulness of viruses having recombinant protein segments is not limited to inducing immunological responses, although an immediate practical use of such viruses is as artificial vaccines. Viruses might, for example, incorporate a protein segment which has an enzymatic or hormonal function. By inducing a controlled, non-pathogenic infection in an animal, a continuous supply of a needed hormonal or enzymatic function might be made available. For example, a virus incorporating a segment of a gonadal hormone might be useful in long-term control of fertility in an animal.

For purposes of further illustrating the invention the following examples are set forth. These examples are not intended to limit the scope of the invention.

EXAMPLE 1

This example is of the construction of a recombinant phage as a carrier of an antigenic site for vesticular stomatis virus (VSV) G protein, which is responsible for attachment of the virus to the host cells in the initial phase of infection. Antibodies to the G protein cause virus neutralization, i.e., abolish infectivity. Amino-acid sequences containing antigenic sites of the G protein are candidates for VSV vaccines.

The purpose of this construction is to introduce the antigenic site of VSV into the D or E subunits of the head coat protein of bacteriophage lambda (which multiplies in *Escherichia coli*) in such a way that the VSV antigenic site is exposed to the outside of the phage coat and accessible to the immune system of a vaccinated animal. The insertion is made in such a way as not to interfere with the assembly of the lambda phage, nor with its infectivity. The constructed lambda phage thus contains the foreign or recombinant protein segment in its protein coat. In this recombinant, the carrier lambda phage contributes the viral stability, ability to reproduce abundantly in simple media and carrier function for immunogenicity; the incorporated protein segment contributing the specific function, i.e., the antigenic site for VSV neutralization.

The construction of the recombinant protein is carried out by in vitro recombination between the DNA of phage lambda and DNA containing the G gene of VSV. The introduction of the DNA segment containing a G antigenic site into lambda phage DNA yields the advantage that the recombinant protein is generated in the regular phage multiplication so that all lambda phage that is produced carries it.

The choice of lambda phage, a bacteriophage that is non-pathogenic to animals, as an appropriate carrier virus for the G gene fragment constitutes step 1 of the general method.

Step 2 involves the insertion of portions of lambda phage DNA into a plasmid which can be easily grown in a cell culture. In lambda phage, the two main proteins constituting the head coat are specified by genes D and E in the 0.11 to 0.15 kb segment of the phage DNA genome from its left end. For simplifying insertion of the VSV sequences, the lambda DNA is fragmented using restriction endonucleases Bam HI and Kpn I. This isolates a fragment between 0.113 and 0.360kb of the phage DNA, including the D and E genes. This fragment is joined to plasmid pBR322 (containing a Kpn I site) which has been cut with Kpn I and Bam HI enzymes. The PBR 322 plasmid with the inserted viral DNA fragment is transformed into a culture of *E coli*, and the recombinant plasmid is reproduced therein as the *E coli* is cultured in a suitable synthetic or broth medium as is well-known in the art. The recombinant plasmid imparts tetracycline-sensitivity and amplicillin-resistance to the transformed *E coli* providing an easy method of selecting *E coli*, cultures infected with recombinant plasmids. Upon lysing positively tested cultures of *E coli*, multiple copies of recombinant pBR322 are released.

The third step is the isolation of the DNA sequence encoding the functional segment of the G VSV protein. The selection of the G VSV gene fragment is based on the known amino-acid sequence, which implicates several base sequences in the determination of antigenic sites. The largest Alu I fragment of the G VSV gene is isolated and then cut with Sau 3a restriction enzyme. The smaller fragment contains one of the antigenic sites, the larger segment two other sites. The latter two sites are further resolved by Hind III digestion.

In the fourth step, the isolated G VSV gene fragments are inserted into the plasmid-bound virus genome fragment after the plasmid-bound fragment is prepared by restriction enzyme digestion. The plasmid is cut by partial digestion with one of a variety of restriction enzymes, which cut lambda phage in the regions of genes D and E, and plasmid DNA with a single cut in those regions are isolated. These single-cut plasmid fragments are recombined with various G VSV gene fragments with appropriate linkers at their ends. Linkers of various lengths are used in order to ensure that at least some of the G VSV gene fragments are placed in the proper reading frame and to allow some flexibility in the recombinant protein. To obtain multiple copies of the recombined plasmids, containing both the viral genome fragments and the G VSV fragment, the plasmids are reproduced by transformation in E coli as per step 2 hereinabove, and multiple copies of the recombined plasmid is obtained from E coli lysate.

Step 5 consists of reconstituting the intact viral genome. The lambda phage DNA fragment is released from the recombinant plasmid by digestion with Kpn I and Bam HI enzymes, and the released fragment is reconnected in two steps, first to the left end Bam HI fragment of phage lambda DNA and then to the right end Kpn I fragment.

The sixth step, in the case of bacteriophage lambda, involves packaging in vitro the reconstituted lambda phage DNA into lambda capsids. The packaging of the phage is carried out in vitro with purified phage extracts according to the method of Sternberg, Tiemeier and Enquist. The recombinant phage is reproduced by infecting cultures of E coli therewith, and the lysing of the E coli releases multiple copies of the recombinant phage.

Finally, recombinant phages are screened by diluting the phage in saline and injecting in rabbits $10^9$–$10^{10}$ virus particles per kilogram of body weight. After 8 days, blood is drawn from the rabbits, and their blood serum is tested by radioimmunoassay for reactivity with G VSV antigen. Reactivity with G VSV antigen demonstrates the production of G VSV antibody by the rabbits, and accordingly, the incorporation of G VSV protein in the phage.

EXAMPLE 2

This is an example utilizing a animal virus carrier appropriate for a human vaccine against another virus which is, in itself, pathogenic. Polio virus vaccines are of two types as presently used. The Salk vaccine consists of chemically crippled polio virus with the inherent risk of a few polio viruses remaining intact in the vaccine and infecting the patient. The Sabin vaccine uses live virus of attenuated strains which have the inherent risk of reverting to pathological form. To produce a safer vaccine, key immunogenic peptide segments can be inserted into a truly safe virus, which can then be used to infect patients without the risks inherent in other vaccines. A suitable nonpathogenic virus suitable is adenovirus type 2 (Ad 2), or vaccine strains of other types.

According to step one of the method, an appropriate protein in Ad 2 capsids is identified. One of the proteins known to be exposed on the surface of adenoviruses is the hexon protein; another is "protein IV" or "fiber". Moreover, the later protein is of various lengths in different strains of adenovirus, and thus some strains must contain regions which can be removed, or substituted for, without reducing infectivity.

The entirety of the Ad 2 genome has been inserted into plasmids in various laboratories. For convenience of further manipulation, the region encoding fiber or hexon is isolated and inserted into another plasmid according to step 2 of the method. The use of fiber will now be pursued. Fiber is known to extend from map units 87 to 91.5 kb. Importantly the fiber-coding region does not overlap messages for other proteins as do other Ad 2 genes. The Hind III "F" fragment (one of the products of the full digestion of Ad 2 DNA with the enzyme Hind III) extends from 89.5 to 97.3 map units. This fragment is isolated first. Ad 2 DNA genome is cut with Hind III, and the products separated on a 1% agarose gel. The fragment of appropriate size is removed by the technique of electroelution.

The plasmid pBR322 is prepared by Hind III digestion and treatment with CIP to prevent religation. The F fragment is then inserted in the plasmid by treatment with T4 DNA ligase. A partial Hind III digestion is performed, and molecules cut only once are purified from a gel. This material is Sma I digested. Sma I cuts at 91 map units, releasing the DNA fragment extending from 91 to 91.3 map units. The fragment from 89.5 to 91 units is still attached to the plasmid. Because Sma I is a "blunt end cutter", the DNA can be directly joined to Hind III linkers. After further Hind III cutting, the plasmid is closed with T4 DNA ligase. The fragment, 89 to 91 map unit fragment, now carried in the plasmid, is entirely within the coding region of Ad 2 fiber (87 to 91.5). The plasmid is transformed into E coli. Ampicillin-resistant, tetracycline-sensitive E coli strains, transformed with recombinant plasmids, are selected, cultured and lysed in order to obtain multiple copies of the recombinant plasmid.

The third step is the isolation of a DNA fragment with a nucleotide base sequence coding for the desired functional protein segment to be attached to the carrier. In this case, the desired function is the ability to stimulate the immune system of a vaccinated human against polio virus. Such a protein segment will be found on the outside of the polio virus. After the virus is fully assembled, a capsid protein, VPO, is cleaved to form two protein segments VP4 and VP2. Since it is accessible to cleavage enzymes, it follows that the amino acids at the VP4-VP2 junctions are on the outermost portions of the virus particle and thus good candidates for immunogenic regions of capsid proteins.

Polio is an RNA rather than a DNA virus. This creates a problem for the technology as described. However, full length DNA copies of the polio RNA genome have now been made by a process known as reverse transcription.

DNA coding for the functional protein segment can be isolated from the DNA, produced by reverse transcription, by a double digest with the restriction enzymes Nru I and Bam HI. A 0.5 kb fragment is purified by electroelution from bisacrylamide gel. The fragment is then further digested into short fragments with Fnn 441 or Mnl I, each of which cuts the fragment in three places.

The small DNA fragments produced, some of which code for the functional protein segments, are prepared for insertion in the phage-bound Ad 2 DNA fragment by blunt ending with Klena or Pol I and then by joining to Bam HI linkers with T4 DNA ligase. Linkers of various sizes are used in order to assure that some fragments will be joined in the proper reading frame in the next step.

The fourth step of the general method involves the joining of the carrier coding DNA to the functional protein segment-coding DNA. The plasmid carrying the Ad 2 fragment is digested very lightly with restriction enzyme Mbo I. Mbo I is a very frequent cutter of the DNA and is used because the best place to incorporate the foreign protein segment is not known in advance. By cutting very lightly, generally, each plasmid-bound Ad 2 fragment is cut one time. Mbo I and Bam HI give compatible ends, and the polio fragments are attached to the Mbo I-cut Ad2 DNA with T4 DNA ligase. Such a joining will not be recut by the enzyme Bam HI. Again, the recombinant plasmid is transformed into *E coli* in order to obtain multiple copies thereof. The Ad 2 genome portions containing the inserted pseudo-polio fragments are excised from the plasmid by digesting the plasmid with Hind III.

In the fifth step, the full Ad2 genome, containing the inserted pseudo-polio fragments, is reconstructed in two steps. First, a partial Sma I digest of intact Ad 2 DNA yields the combined G-K Sma I fragment (the right arm), which can be purified. Because Sma I is a blunt end cutter, Hind III linkers are directly attached thereto with T4 DNA ligase at the side cut by Sma I. The left side is the end of the viral DNA and is uncut. This plasmid DNA is Hind III-cut, and the polio DNA-containing Ad 2 viral genome is isolated from the plasmid fragment by electrophoresis. The viral genome fragment is attached to the prepared Ad 2 arm with T4 DNA ligase, half of the molecules being of the correct orientation. The other required Ad 2 arm is prepared by partial Hind III digestion and isolation of the combined G-E-C-H-D-A-B Hind III fragment. This is then attached to the recombinant polio DNA-containing Ad 2 fragment on the free side generating Ad 2 genomes, one-half having a configuration with potential virus-producing capabilities.

In the sixth step, the recombinant Ad 2 genomes are transfected into Hela cells by phosphate calcium coprecipitation, and the transfected Hela cells are cultured in DME medium with 10% horse serum. Only viruses having all of the genes necessary for virus viability and reproduction, in correct reading frame, generate the viral protein coat and cause lytic infection of the Hela cells to produce progeny viruses. Some of these reconstructed viruses also incorporate polio virus DNA fragments which are expressed in the fiber protein of the Ad 2 virus.

Which of the recombinant viruses incorporate polio virus proteins in an exposed manner is determined by injecting rabbits with various viral fractions to determine whether the rabbits produce antibodies to polio virus. Rabbits are injected with $10^9$–$10^{10}$ particles of recombinant Ad 2 virus, diluted in saline, per kilogram of body weight. After 8 days, blood is drawn. Reactivity of the blood serum with polio virus is determined by radioimmunoassay. Recombinent Ad 2 virus, incorporating polio virus protein as established by antibody induction in rabbits, has potential as a safer human polio vaccine.

While the invention has been described in terms of certain preferred embodiments, modifications obvious to one with ordinary skill in the art may be made without departing from the scope of the invention. For example, while the invention has been described in terms of inserting DNA nucleotide sequences into viral genomes, an RNA nucleotide sequence would be inserted in viruses which have an RNA genome, working through DNA intermediates, and such recombinant RNA viruses are within the scope of the invention.

Various features of the invention are emphasized in the following claims.

What is claimed is:

1. A method of modifying a virus to give the virus a new biological function comprising inserting a foreign nucleotide base sequence into the viral genome at a location whereat said foreign nucleotide base sequence expresses itself as an exposed segment of a surface viral protein, which surface viral protein forms a part of the coat of the modified virus.

2. A method according to claim 1 further comprising examining the known molecular biology of said virus and choosing a surface viral protein which, according to its molecular biology, is not critical to the reproductive viability of said virus or a portion of a surface protein which, according to the molecular biology of said virus, is not critical to the reproductive viability of said virus, and inserting said foreign nucleotide base sequence into the viral genome at a location whereat said foreign nucleotide base sequence is expressed as an exposed segment of said noncritical surface protein or of said noncritical portion of a surface protein.

3. A method according to claim 1 wherein said foreign nucleotide base sequence is inserted into said genome by splicing into a cloning vector a portion of said viral genome containing at least a fragment of the gene for said surface protein, infecting an organism with said spliced cloning vector to obtain multiple copies of said spliced cloning vector, cleaving said spliced cloning vector at a location within said surface protein gene fragment, linking said foreign nucleotide base sequence to the cleaved ends of said surface protein gene fragment, isolating said spliced portion of said viral genome portion containing said foreign nucleotide base sequence, from said cloning vector, and joining said isolated genome portion with additional viral genome portions necessary to create a functional viral genome.

4. A method according to claim 3 further comprising packaging said viral genome, containing said foreign nucleotide base sequence, as a complete virus.

5. A method of modifying a virus to produce a modified virus for introduction into a live animal comprising selecting for modification a virus which is known to be non-pathogenic in the animal into which said modified virus is to be introduced, and inserting a foreign nucleotide base sequence into the viral genome of said selected virus at a location whereat said foreign nucleotide base sequence is expressed as an exposed segment of a surface viral protein, which expressed surface viral protein forms a part of the coat of the modified virus.

6. A method of producing an agent which induces an immunological response in an animal comprising choosing a known immune-response-inducing segment of a protein, isolating a nucleotide base sequence which codes for said protein segment, inserting said isolated nucleotide base sequence into the genome of a virus at a location whereat said nucleotide base sequence is expressed as an exposed segment of a viral surface protein without disrupting reproductive viability of said virus which surface viral protein forms a part of the coat of the virus.

7. A method of producing an agent according to claim 6 wherein a nucleotide base sequence is inserted into the genome of a virus that is non-pathogenic to an animal, whereby said agent is useful as a vaccine.

8. A method of producing a modified virus which carries an exposed segment of a foreign protein, which segment is known to be immunologically active within an animal into which the modified virus is to be introduced, the method comprising selecting a virus for modification which is non-pathogenic in the animal, examining the known molecular biology of said selected virus and choosing a surface protein of said virus which, according to its molecular biology, is not critical to the reproductive viability of said virus or a portion of a surface protein which, according to the molecular biology of said virus, is not critical to the reproductive viabliity of said virus, splicing into a cloning vector a portion of the genome of said virus which contains at least a fragment of the gene that encodes said surface protein, transforming a microorganism with said spliced cloning vector to obtain multiple copies of said spliced cloning vector, choosing a known immune-response-inducing segment of a protein that is foreign to said virus, isolating a nucleotide base sequence which encodes said foreign protein segment, cleaving said spliced cloning vector at a location within said surface protein-encoding genome portion, linking said foreign nucleotide base sequence to the cleaved ends of said surface protein-encoding genome portion, isolating said linked viral genome portion containing said foreign nucleotide base sequence from said cloning vector, joining said isolated genome portion to additional viral genome portions necessary to create a functional viral genome, and packaging said functional viral genome, containing said foreign nucleotide base sequence, as a complete virus.

* * * * *